(12) United States Patent
Schoeder et al.

(10) Patent No.: US 10,888,305 B2
(45) Date of Patent: Jan. 12, 2021

(54) RECEIVING DEVICE AND METHOD FOR OBTAINING A SALIVA SAMPLE

(71) Applicant: BOEHRINGER INGELHEIM VETMEDICA GmbH, Ingelheim am Rhein (DE)

(72) Inventors: Heinz Schoeder, Ingelheim am Rhein (DE); Christoph Weber, Ingelheim am Rhein (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 237 days.

(21) Appl. No.: 15/576,764

(22) PCT Filed: Jun. 8, 2016

(86) PCT No.: PCT/EP2016/025055
§ 371 (c)(1),
(2) Date: Nov. 24, 2017

(87) PCT Pub. No.: WO2016/198167
PCT Pub. Date: Dec. 15, 2016

(65) Prior Publication Data
US 2018/0303467 A1    Oct. 25, 2018

(30) Foreign Application Priority Data
Jun. 8, 2015    (DE) .......................... 10 2015 007 098

(51) Int. Cl.
*A61B 10/00*    (2006.01)
*A01K 29/00*    (2006.01)

(52) U.S. Cl.
CPC .......... *A61B 10/0051* (2013.01); *A01K 29/00* (2013.01); *A61B 10/0096* (2013.01)

(58) Field of Classification Search
USPC ........................................................ 600/573
See application file for complete search history.

(56) References Cited

U.S. PATENT DOCUMENTS

| 5,910,122 A | 6/1999 | D'Angelo |
| 9,744,014 B2 | 8/2017 | Smith et al. |

(Continued)

FOREIGN PATENT DOCUMENTS

| AU | 2014200325 A1 | 8/2014 |
| CN | 203700242 U | 7/2014 |
| GB | 2 392 244 A | 2/2004 |

OTHER PUBLICATIONS

Tierra Smiley, D.V.M. et al., Noninvasive Saliva Collection Techniques for Free-Ranging Mountain Gorillas and Captive Eastern Gorillas, Journal of Zoo and Wildlife Medicine, vol. 41, No. 2, Jun. 2010, p. 201-209, XP002760595, ISSN: 1042-7260 Chapter "Dental Rope Saliva Collection Techniques".

*Primary Examiner* — Christian Jang
*Assistant Examiner* — Mitchell E Alter
(74) *Attorney, Agent, or Firm* — David S. Safran; Roberts Calderon Safran & Cole, P.C.

(57) ABSTRACT

A receiving device for receiving saliva from an animal, having a core and a casing, as well as a kit with a receiving device and a collecting device, wherein the core can be removed from or pulled out of the receiving device to allow examination of the saliva. In addition, a method of using the core of a rope for obtaining a saliva sample from an animal, particularly a pig, wherein saliva is filtered during the sampling by means of the casing of the rope or a receiving device and/or after the sampling the core of the rope or a core of the receiving device is removed from or pulled out of the casing to allow examination of the saliva.

13 Claims, 4 Drawing Sheets

(56) References Cited

U.S. PATENT DOCUMENTS

2003/0082528 A1    5/2003   Smith et al.
2007/0062460 A1*   3/2007   Simer ................... A01K 29/00
                                                                             119/709

* cited by examiner

RECEIVING DEVICE AND METHOD FOR OBTAINING A SALIVA SAMPLE

BACKGROUND OF THE INVENTION

Field of the Invention

The present invention relates to a receiving device for receiving/absorption saliva from an animal, particularly a pig, having a core and a casing, the casing at least substantially surrounding the core, a kit for obtaining a filtered saliva sample from an animal, in which the receiving device is combined with a collecting device or bag, and a method for obtaining a saliva sample from an animal, particularly a pig, using the receiving device and a collecting device.

Description of Related Art

Saliva and/or liquid from the oral cavity of an animal contains, among other things, water, proteins, electrolytes, mucus, serum and serum components, blood cells, mucous membrane cells as well as microorganisms and antibodies.

For the veterinary examination of animals, particularly domesticated mammals, such as pigs, cows, goats, sheep or the like, it is conventional to examine the saliva or oral cavity liquid of the animal for diseases and/or pathogens. Diseases and/or pathogens can be detected in particular by the detection of antibodies and/or microorganisms, such as bacteria, viruses and/or fungi in the saliva of the affected animal.

The taking of saliva or oral cavity liquid from an animal, particularly a pig, in order to obtain a sample for analysis or a saliva sample, is carried out, for example, as described in U.S. Patent Application Publication 2003/0082528 A1 using a receiving device such as a rope or cord. Preferably, the saliva is taken up or absorbed by the receiving device by oral contact between the animal and the receiving device, particularly by chewing and/or biting. Then the saliva or sample material taken is separated from the receiving device, for example, by wringing out the receiving device. The saliva sample thus obtained is then subjected to examination by a veterinary specialist.

U.S. Patent Application Publication 2007/0062460 A1 discloses a method for obtaining a saliva sample from a pig by means of a saliva-absorbing receiving device, such as a rope, in which, according to a preferred embodiment, the receiving device comprises a core and a water-permeable protective casing which protects the core from wear.

The above-mentioned method for obtaining a saliva sample from an animal has the disadvantage, however, that the quantity and/or quality of the saliva sample obtained in this way is often inadequate for the subsequent veterinary examination. In addition to the contaminants already present in the saliva, the sample material taken may be further contaminated by the handling of the receiving device at the sampling site. This adversely affects the subsequent veterinary examination and/or requires complex working up of the resulting saliva sample in the laboratory.

SUMMARY OF THE INVENTION

Against this background, the present invention sets out to solve the problem of providing an improved receiving device for receiving saliva from an animal and an improved method for obtaining a saliva sample from an animal, preferably enabling or assisting with a simple, safe, inexpensive, hygienic and/or rapid taking of saliva or obtaining of a saliva sample, reducing contamination during and/or after the taking of saliva or obtaining of a saliva sample, and/or enabling the saliva sample to be examined directly or immediately by a veterinary specialist, preferably without any further processing.

The above problem is solved by a receiving device, a kit, and a method as described herein.

By the term "sample material" is preferably meant, according to the present invention, the saliva taken from the animal during testing. Particularly preferably, the sample material is the saliva taken from the animal by means of the receiving device or the saliva absorbed by or adhering to the receiving device. The sample material preferably comprises saliva and/or consists predominantly of saliva. However, the sample material may also contain contaminants or particles such as food residues, dust, fecal traces or the like. Preferably, the sample material is the starting material for a saliva sample and/or the sample material is processed, particularly eluted, in order to obtain or prepare a saliva sample.

By the term "saliva sample" is preferably meant, according to the present invention, the sample material which has been processed, particularly eluted. In particular, the saliva sample can be analyzed and/or fed into an analyzer immediately or directly and/or without any further processing.

The proposed receiving device for taking up saliva from an animal, particularly a pig, preferably comprises a core and a casing/shell, the casing/shell at least substantially surrounding the core, preferably completely and/or over the complete length of the core.

By the term "receiving device" is preferably meant, according to the present invention, a construction which is configured particularly to remove saliva from the animal, by preferably oral contact with an animal, particularly by chewing and/or biting of the receiving device, and/or for sucking up and/or absorbing saliva and/or sample material from the animal and/or for preparing a saliva sample. Particularly preferably, the receiving device is embodied as a rope, cord or the like.

In one aspect of the present invention, a core of the receiving device can be removed or pulled out from the receiving device or a casing of the receiving device, preferably at least substantially non-destructively, preferably after oral contact with the animal and/or for examining the saliva and/or for processing the sample material taken and/or for obtaining a saliva sample. This makes it possible to obtain a saliva sample in a particularly simple, fast, hygienic and/or inexpensive manner. In particular, in this way, contaminants adhering to or in the casing of the receiving device can be separated from the core or from the sample material taken up by the core of the receiving device. This helps with the subsequent examination of the sample material or saliva sample. In particular, a receiving device of this kind makes it possible to carry out direct filtration of the sample material during sampling or when it comes into oral contact with the animal, particularly by dispensing with the need for further processing or filtration of the saliva or sample material for the subsequent veterinary examination.

According to a particularly preferred embodiment, the receiving device is embodied as a rope, preferably wherein the core is embodied as a core of the rope which can preferably be pulled out completely or partially. This allows a particularly simple, fast and/or inexpensive taking of saliva or obtaining of a saliva sample.

In another aspect which can also be implemented independently, the present invention relates to a kit for obtaining a filtered saliva sample from an animal, particularly a pig, with a proposed receiving device, a collecting device, particularly a bag, and optionally instructions for use. Preferably, using the kit, it is possible to obtain a saliva sample from the animal which is filtered and suitable for immediate or direct analysis.

A kit in the sense of the present invention is, in particular, a combination and/or a system comprising the proposed receiving device and a collecting device. Preferably, the receiving device and the collecting device each form a component of the kit. The components of the kit are preferably sold in combination, particularly in a combined pack or the like. However, it is also possible for the above-mentioned components to be provided loose for using together. Preferably, a common or linking element is provided, such as, for example, instructions for use, handling recommendations or information in the text on one or more of the components of the kit or on the common packaging.

By the term "collecting device" is preferably meant, according to the present invention, a construction which is embodied in particular to at least temporarily store biological material and/or fluids such as saliva, keep them away from the environment and/or collect them. Particularly preferably, a collecting device according to the present invention is a container, a reservoir, a bag, a funnel and/or a vessel. Most particularly, in a collecting device according to the present invention, saliva or the sample material taken from the animal by means of the receiving device can be separated from the receiving device, particularly dissolved or eluted out of it, wrung out, squeezed out and/or removed by centrifuging.

In the proposed method for obtaining an, in particular, filtered saliva sample from an animal, particularly a pig, saliva from the animal is taken up or absorbed by a receiving device, particularly a rope, preferably by oral contact with the animal.

According to another aspect of the present invention which can also be implemented independently, the saliva or the sample material taken up can be filtered—particularly immediately or directly—during the sampling by means of the receiving device, particularly a casing of the receiving device. In particular, contaminants or particles of the saliva or the sample material taken are separated from the receiving device, particularly from a casing of the receiving device, by the fact that the filtered saliva or filtered sample material is taken up or absorbed by a core of the receiving device. This guarantees or assists with the obtaining of a filtered saliva sample in a particularly efficient, simple, fast and/or inexpensive manner.

According to another aspect of the present invention which can also be implemented independently, after the sample taking or oral contact with the animal the core of the receiving device is removed or pulled out from the receiving device or a casing of the receiving device, particularly for further examination of the saliva or sample material taken up or absorbed by the core. This ensures or assists with a particularly simple, fast and/or inexpensive separation of the core from the casing of the receiving device, or removal of contaminants.

The use of the core of a rope to obtain an, in particular, filtered saliva sample from an animal, particularly a pig, according to the invention, proposes that saliva from the animal be taken up in particular by oral contact with the animal by means of the rope and that it be filtered by means of the casing of the rope and then the core of the rope comprising the filtered saliva or the filtered sample material be removed or pulled out from the rope or the casing of the rope for examination of the saliva or sample material. This has corresponding advantages.

By the term "rope" is preferably meant, according to the present invention, an elongate object which is embodied particularly for transmitting tensile forces. According to this meaning, a rope is, in particular, at least substantially axially rigid, flexible and/or elastic. Preferably, a rope is a plaited, woven or knitted structure, particularly made from fibers, or particularly preferably comprises such a structure as its casing.

Additional advantages, features, properties and aspects of the present invention will become apparent from the following description of a preferred embodiment with reference to the accompanying drawings.

DETAILED DESCRIPTION OF THE INVENTION

Figure 1:
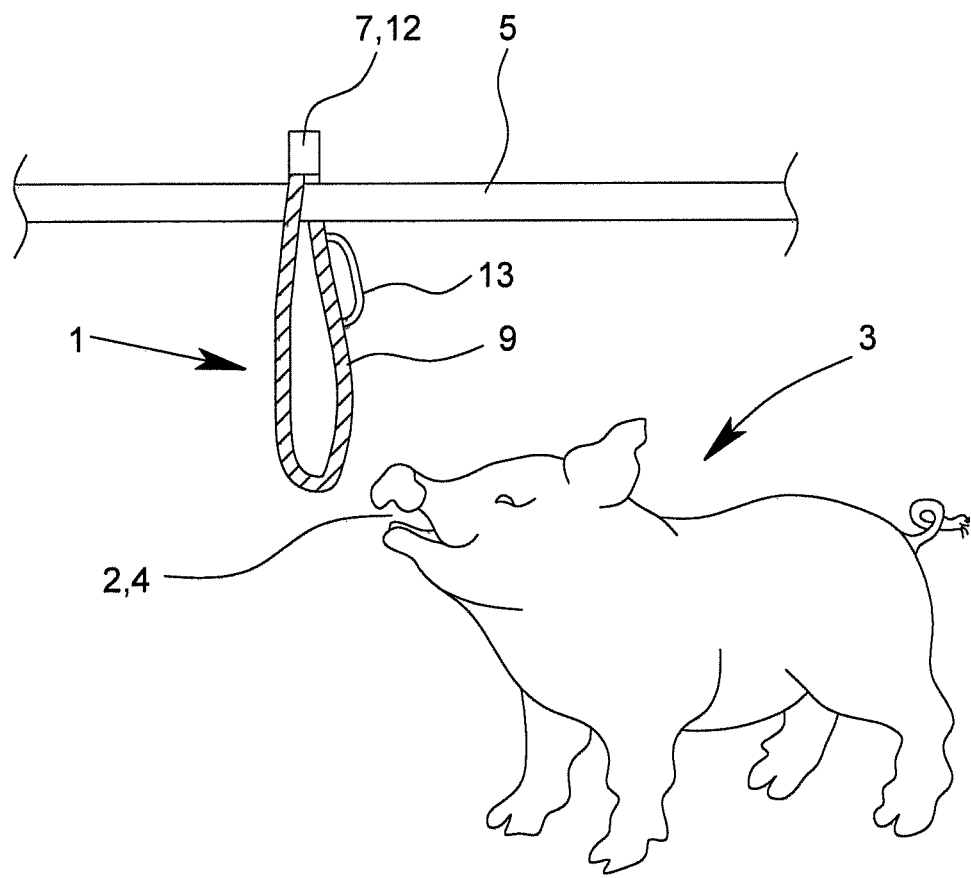
FIG. 1 is a schematic view of a proposed receiving device and its use for obtaining a saliva sample from an animal.

In the figures, which are purely schematic and not to scale, the same reference numerals have been used for identical or similar parts resulting in corresponding or comparable properties and advantages, even if there is no repetition of the related description.

FIG. 1 shows a receiving device 1 or the use of a receiving device 1 according to a particularly preferred embodiment.

The receiving device 1 is preferably configured to receive/absorb saliva 2 from an animal 3. FIG. 1 shows, by way of example, the use of the receiving device 1 on a pig. However, the receiving device 1 may also be used to collect saliva 2 from other, particularly domesticated, animals 3.

The receiving device 1 is preferably at least substantially elongated, in the shape of a rod or ball. Particularly preferably, the receiving device 1 is at least partially in the form of a rope or cord, as shown in particular in FIG. 1. However, other solutions or embodiments are also possible. In particular, the receiving device 1 may be at least substantially spherical, annular or cylindrical or at least partially in the form of a ball, ring or cylinder.

Preferably, the receiving device 1 is longer than 20 cm or 30 cm, particularly preferably longer than 40 cm or 50 cm, particularly longer than 80 cm or 100 cm, and/or shorter than 10 m or 8 m, particularly preferably shorter than 6 m or 4 m, particularly shorter than 3 m or 2 m.

Preferably, the receiving device 1 is at least substantially flexible, elastic, tear-resistant and/or or bite-proof. Particularly preferably, the receiving device 1 is configured to be at least partially and/or temporarily received, chewed and/or bitten in the mouth 4 of the animal 3.

Preferably, the receiving device 1 has a tensile strength of more than 100 $N/mm^2$, particularly preferably more than 200 $N/mm^2$, particularly more than 300 $N/mm^2$, and/or less than 1000 $N/mm^2$, particularly preferably less than 900 $N/mm^2$ or 800 $N/mm^2$, particularly less than 750 $N/mm^2$.

The tensile strength is preferably the maximum mechanical tensile stress that can be loaded onto the receiving device 1 without it tearing. The tensile strength is preferably determined in the course of a tensile test, preferably according to ISO 5079, ISO 2062 and/or ISO 6939.

The receiving device 1 is preferably adapted to be attached, particularly suspended, in a stall (not shown). In the embodiment shown, the receiving device 1 is attached to or suspended from a carrier 5. However, it is also possible to make the receiving device 1 accessible to the animal 3 in some other way.

Particularly preferably, a loop may be formed or shaped from the receiving device 1. This enables the receiving device 1 to be mounted particularly easily, quickly and/or securely.

Preferably, the ends 6 of the receiving device 1 are connected, or connectable, to one another by means of a connecting element 7, which may, in particular, be releasable or cuttable. The connecting element 7 is preferably configured as an adhesive strip or whipping, i.e., a cord or twine used to bind or cover a rope.

The receiving device 1 preferably comprises a core 8 and a casing 9, while the casing 9 particularly surrounds the core 8 at least substantially—particularly, in the radial direction, completely and/or over the complete length of the core 8.

Particularly preferably, the core 8 is separated from the environment or protected from direct contact with the environment or with the animal 3 by the casing 9, in particular entirely and/or to all sides.

Figure 2:
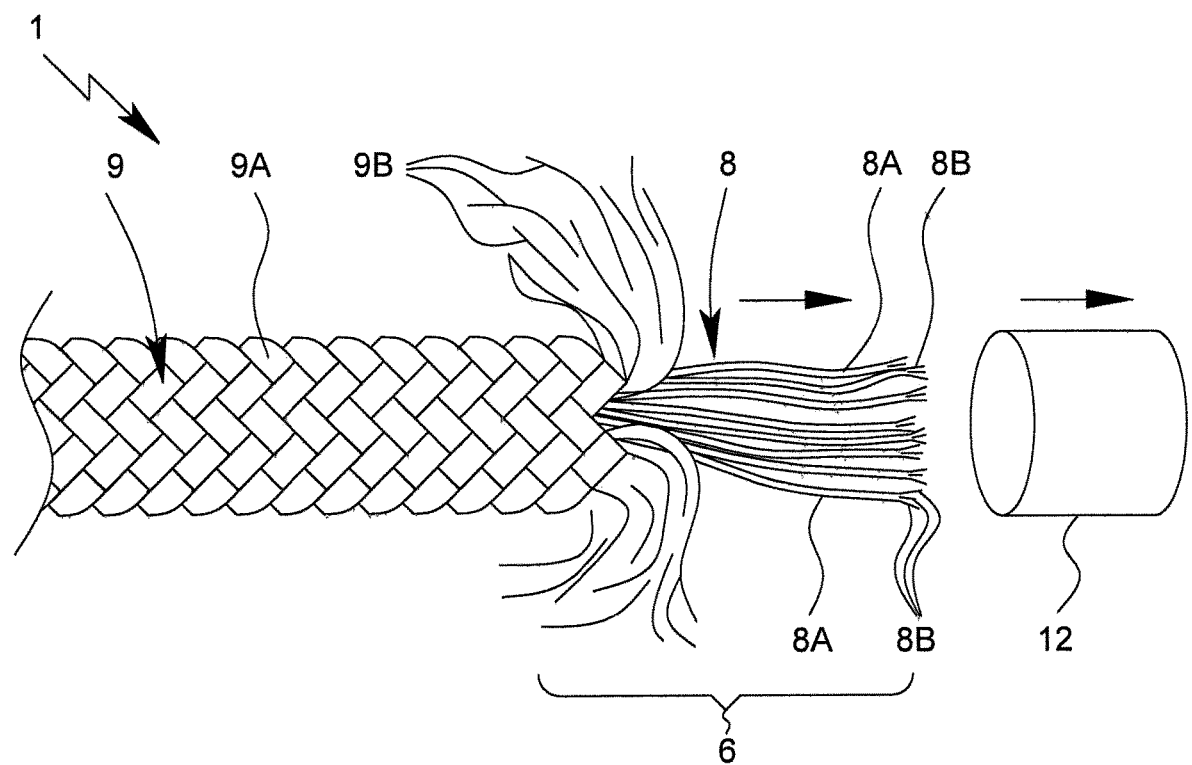
FIG. 2 is a schematic view of the receiving device according to FIG. 1 with the core partially pulled out.
Figure 3:
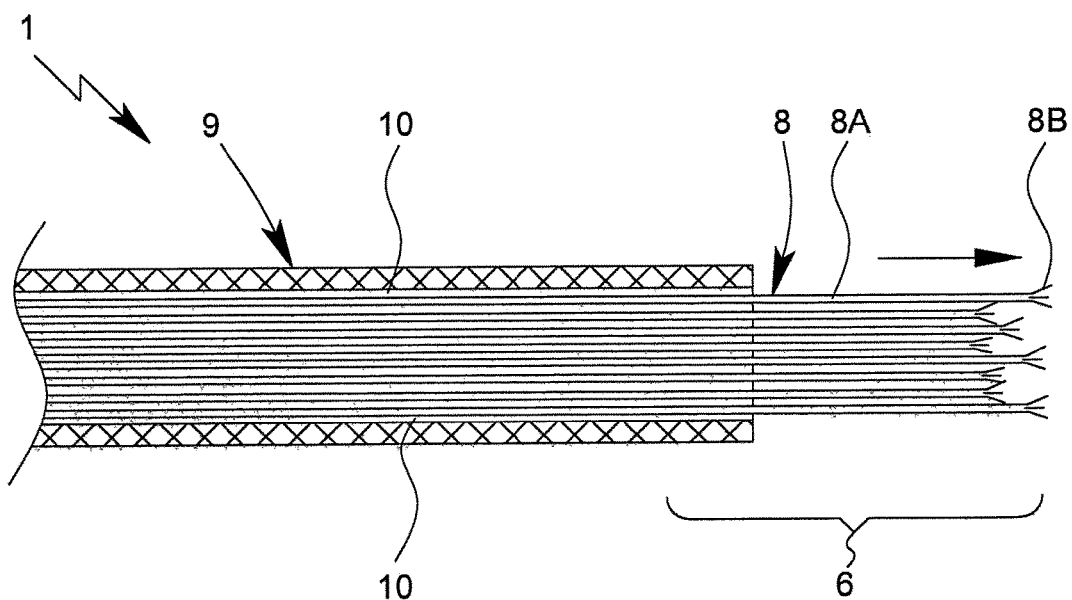
FIG. 3 is a schematic section through the receiving device according to FIG. 2.
Figure 4:
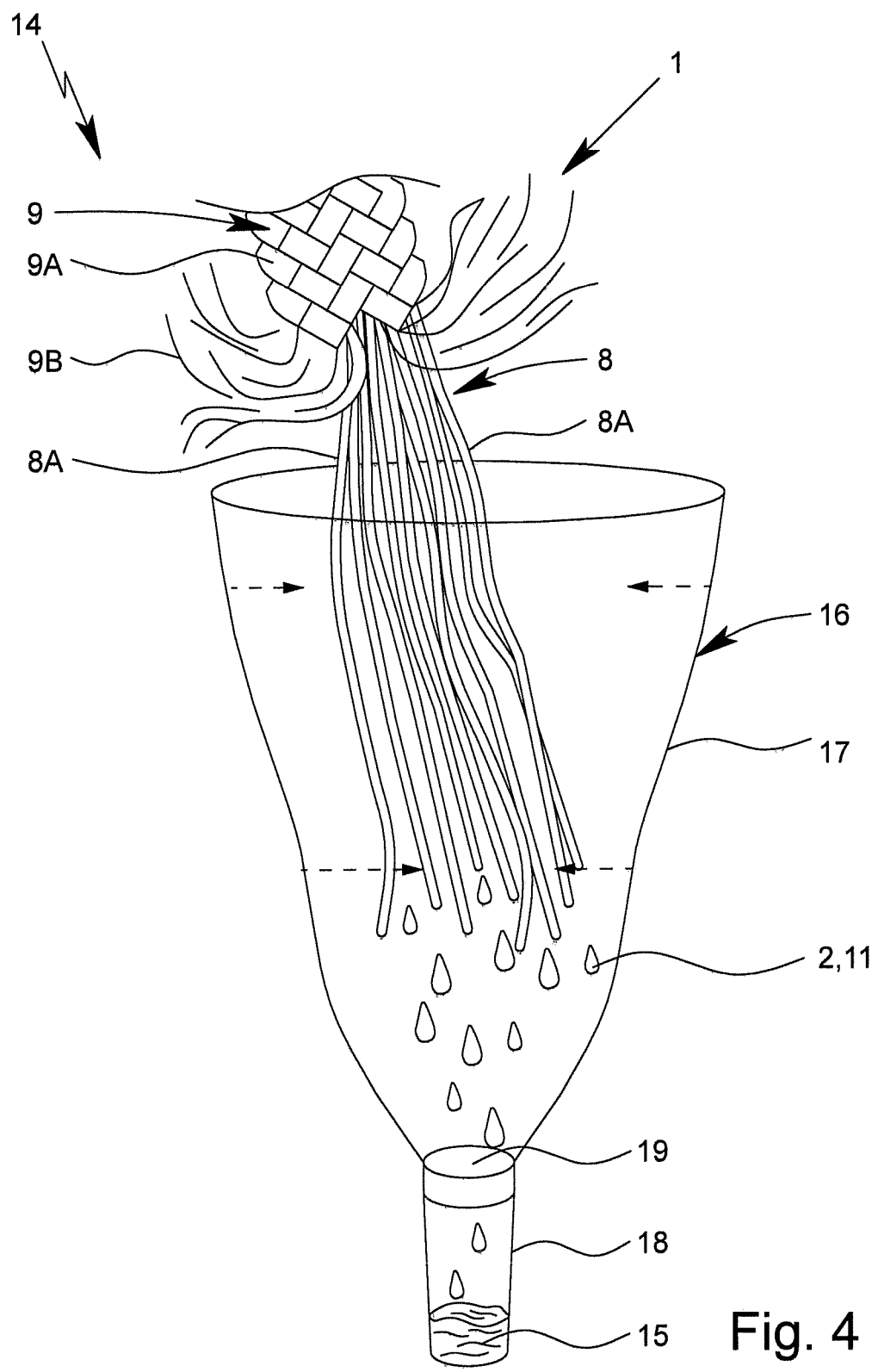
FIG. 4 is a schematic view of a proposed use of elements of a kit comprising the receiving device according to FIG. 2 and a collecting device.
Figure 5:
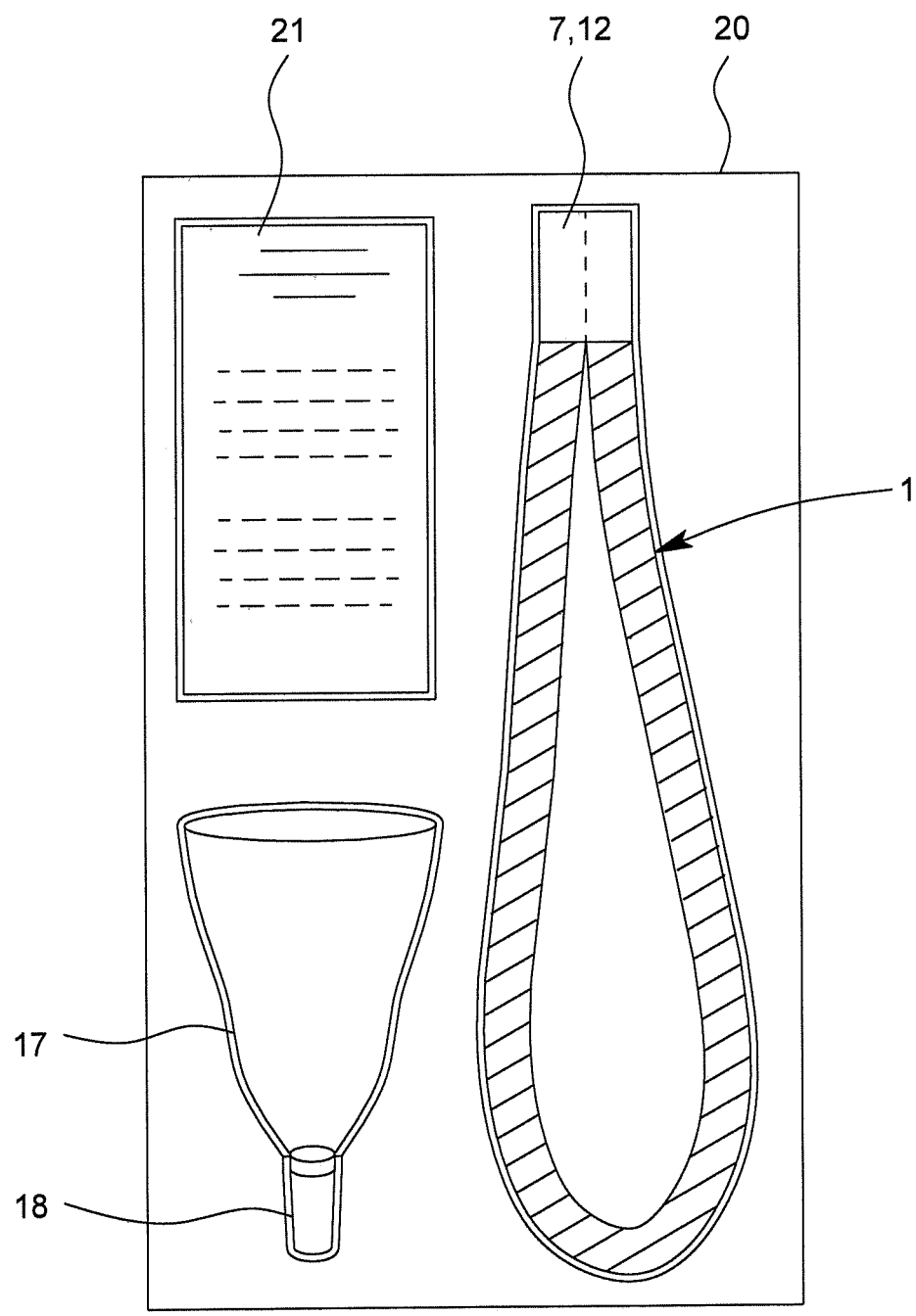
FIG. 5 shows a kit in accordance with the invention.

As can be seen from FIGS. 2 to 4, in particular, the core 8 of the receiving device 1 is preferably configured as an extractable or removable core or insert of the receiving device 1.

Preferably, the core 8 is loosely or displaceably contained within the casing 9 or held by the casing 9. Most preferably, the outer diameter of the core 8 is smaller than the inner diameter of the casing 9. Preferably, some play or clearance 10 is provided between the core 8 and the casing 9, particularly so that the core 8 can be pulled out or removed from the casing 9 in at least substantially frictionless manner.

Preferably, the thickness of the casing 9 is less than the width or diameter of the core 8. Preferably, the thickness of the casing 9 is less than 50%, particularly preferably less than 20% or 30%, particularly less than 5% or 10%, of the width or diameter of the core 8. In a most particularly preferred embodiment, the thickness of the casing 9 is less than 2% of the width or diameter of the core 8.

Preferably, the play or clearance 10 is more than 0.5 mm or 0.8 mm, particularly preferably more than 1 mm or 1.2 mm, particularly more than 1.5 mm or 2 mm, and/or less than 5 mm or 4 mm, particularly preferably less than 3 mm or 2 mm.

Preferably, the sliding coefficient of friction between the core 8 and the casing 9 is less than 0.5 or 0.4, particularly preferably less than 0.3 or 0.2, particularly less than 0.1.

Preferably, the adhesive friction and/or the sliding friction between the core 8 and the casing 9, particularly for the purpose of, or during, the pulling out or removal of the core 8 from the casing 9, is less than 1000 N or 800 N, particularly preferably less than 300 N or 100 N, particularly less than 50 N or 10 N. This enables the core 8 to be removed from the casing 9 particularly easily.

Preferably, the casing 9 is at least substantially pervious or permeable to water, particularly such that saliva 2 or sample material 11 which preferably contains saliva 2 from the animal 3 and which has been absorbed or taken up by the receiving device 1, is able to flow inwards through the receiving device 1 or casing 9.

Preferably, the receiving device 1 or the casing 9 of the receiving device 1 comprises a plurality of openings through which the saliva 2 or the sample material 11 can flow. Particularly preferably, the openings in the casing 9 are provided by a plaited material. However, it is also possible for the openings in the casing 9 to be formed by bores, slots or the like.

Most preferably, the casing 9 is configured as a filter or sieve and/or configured to filter the saliva 2 or the sample material 11 taken up, on the one hand, and separate off particles or contaminants, on the other hand.

Preferably, the particles or the contaminants in the saliva 2 or the sample material 11 that is to be purified are deposited on the surface of and/or inside the casing 9.

Preferably, the openings in the casing 9 each have a width or a diameter of less than 2000 µm or 1500 µm, particularly preferably less than 1000 µm or 750 µm, particularly less than 500 µm or 250 µm. Preferably, particles or contaminants with a size or maximum diameter of more than 2000 µm or 1500 µm, particularly preferably more than 1000 µm or 800 µm, particularly more than 500 µm or 200 µm, can be deposited by means of the casing 9, particularly on the surface of and/or inside the casing 9.

Preferably, the core 8 is configured as an absorber and/or the core 8 absorbs fluids, particularly saliva 2 or sample material 11, more strongly, particularly more rapidly, than the casing 9. In particular, the rate of absorption or the coefficient of absorption of the core 8 is greater than the rate of absorption or the coefficient of absorption of the casing 9.

Preferably, the uptake of water of the core 8 and/or casing 9 is more than 1% or 2%, particularly preferably more than 5% or 8%, most preferably more than 10% or 15%, particularly more than 20% or 30%. The uptake of water is preferably the quotient of the mass of the saliva taken up by the core 8 and/or casing 9 in relation to the mass of the (completely dry) core 8 and/or casing 9.

Preferably, the core 8 is configured to absorb more saliva 2 or sample material 11 than the casing 9. Preferably, more than 50% or 60%, particularly preferably more than 70% or 80%, particularly more than 90% or 95%, of the total amount of saliva 2 or sample material 11 which can be taken up or absorbed by the receiving device 1 can be taken up or absorbed by means of the core 8. This assists with, or makes it possible, to achieve a particularly high yield by the sampling process and/or to obtain a saliva sample in a particularly efficient manner.

Preferably, the core 8 and the casing 9 are made from the same material or substance, or the core 8 and the casing 9 comprise the same material or the same substance.

Preferably, the receiving device 1, particularly the core 8 and/or the casing 9, is or are biodegradable and/or digestible or can be broken down by digestive enzymes. This removes or reduces potential damage to the health of the animal 3 and/or ensures that the receiving device 1 or constituents of the receiving device 1 is or are tolerated by the animal 3, in the event that the animal 3 eats the receiving device 1 or parts of the receiving device 1.

Particularly preferably, the receiving device 1, particularly the core 8 and/or the casing 9, comprise(s) natural fibers such as cotton, linen, hemp, coconut and/or sisal and/or the receiving device 1, particularly the core 8 and/or casing 9, is or are formed thereby. However, it is also possible for the receiving device 1, particularly the core 8 and/or the casing 9, to comprise synthetic fibers, such as polyester, polyamide, polypropylene and/or polyethylene, and/or to be formed thereby.

Preferably, the core 8 comprises at least one strand, cord or string 8A and/or the core 8 is formed by at least one strand, cord or string 8A. In the embodiment shown, the core 8 comprises a plurality of strands 8A or the core 8 is formed by a plurality of strands 8A, the strands 8A preferably being arranged at least substantially parallel to one another and/or untwisted in the casing 9. The strands 8A are preferably formed by a plurality of threads 8B that are, in particular, twisted or twined together. However, it is also possible for the core 8 to be formed in one piece.

Preferably, the casing 9 comprises at least one strand, cord or string 9A and/or the casing 9 is formed by at least one strand, cord or string 9A. In the embodiment shown, the casing 9 comprises a plurality of strands 9A, the strands 9A preferably being twisted, whipped or plaited together. The strands 9A are preferably formed by a plurality of threads 9B that are, in particular, twisted or twined together. However, it is also possible for the casing 9 to be formed in one piece.

As shown particularly in FIG. 2, the receiving device 1, particularly the casing 9, can be opened, preferably non-destructively.

Preferably, the receiving device 1 has, particularly in the end position or at one or both ends 6, a closure element 12, such as a cap or a cover, the closure element 12 preferably closing off the casing 9, particularly at its end or axially. Particularly preferably, the closure element 12 is connected to the receiving device 1 or casing 9 in interlockingly, frictionally or materially connected manner, particularly by adhesive bonding.

Optionally, the connecting element 7 forms the closure element 12 or vice versa.

Preferably, the receiving device 1 can be opened by removing, particularly pulling or twisting off, the closure element 12, particularly so that the core 8 can be—partially or completely—removed or pulled out from the casing 9.

Preferably, the core 8 projects partially from the casing 9 or the core 8 is exposed at its end, preferably so that it can be gripped after the release of the closure element 12. This provides a simple and/or fast means of removing the core 9 from the casing 9.

Additionally, or alternatively, the casing 9 can be cut or torn open in order to remove the core 8.

As illustrated in FIG. 1 in particular, the receiving device 1 preferably has a handle 13, the handle 13 being, in particular, arranged on the receiving device 1 or on the casing 9 or connected to the casing 9. Particularly preferably, the handle 13 is formed in one piece with the casing 9 and/or is spliced onto the receiving device 1, particularly the casing 9. Most preferably, the handle 13 is configured as a lateral loop or eyelet spliced onto the casing 9.

Preferably, the receiving device 1 can be held by a user (not shown) by means of the handle 13—particularly during the extraction or removal of the core 8. This method of construction enables the receiving device 1 to be held by the handle 13, without exerting any pressure on the casing 9 and/or the core 8. This facilitates the extraction or removal of the core 8 from the casing 9.

FIG. 4 shows use of elements of a proposed kit 14 for obtaining a filtered saliva sample 15, the kit 14 preferably comprising at least the receiving device 1 and a collecting device 16, but also can include instructions for use 21 within a packaging 20.

The collecting device 16 is preferably configured to at least partially accommodate the receiving device 1, particularly the core 8 of the receiving device 1. In particular, the receiving device 1 or the core 8 can be placed in the collecting device 16.

In the embodiment shown, the collecting device 16 is embodied as a funnel or is at least partially funnel-shaped. However, other solutions are also possible.

Preferably, the collecting device 16 comprises an, in particular, flexible bag 17 and/or the collecting device 16 is configured as an, in particular, flexible bag 17. Additionally, or alternatively, the collecting device 16 comprises an, in particular, rigid container 18 and/or the collecting device 16 is configured as an, in particular, rigid container 18.

Preferably, the bag 17 is connected to the container 18 by interlocking, frictional and/or material engagement, particularly by adhesive bonding. In particular, the container 18 can be separated or removed from the bag 17.

In the embodiment shown, the bag 17 is fluidically connected to the container 18 by means of an opening 19.

Preferably, the collecting device 16 or the bag 17 is flexible, elastic and/or deformable so that the receiving device 1 or the core 8 can be wrung out, squeezed out and/or pressed out in the collecting device 16 or in the bag 17, particularly manually. In particular, by compressing the collecting device 16 or the bag 17, the receiving device 1 or the core 8 can be wrung out, squeezed out and/or pressed out, preferably so that the saliva 2 or the sample material 11 is released from the receiving device 1 or the core 8 and collects in the collecting device 16, particularly the container 18.

The proposed method of using the core of a rope for obtaining the filtered saliva sample 15 of the animal 3 is explained in more detail hereinafter.

The proposed method is preferably carried out by means of the receiving device 1 or the kit 14.

Preferably, the receiving device 1 or the rope with the removable core is made available to the animal 3, particularly by allowing preferably oral contact of the receiving device 1 or of the rope with the animal 3 or the mouth 4 of the animal 3.

Preferably, the receiving device 1 or the rope is secured in a stall (not shown) by interlocking, frictional and/or material engagement, preferably on the carrier 5. Most preferably, the receiving device 1 or the rope is arranged or mounted in a suspended position in a stall, as shown in FIG. 1, in particular.

Preferably, saliva 2 from the animal 3 is taken up, particularly absorbed, by the receiving device 1 or the rope, particularly as a result of, in particular, oral contact with the animal, particularly by chewing and/or biting of the receiving device 1 or rope.

Preferably, the saliva taken up or absorbed or the sample material 11 thus taken from the animal 3 penetrates or flows through the casing 9 of the receiving device 1 or rope. Particularly preferably, the saliva 2 or the sample material 11 that has been taken up or absorbed is filtered by means of the casing, particularly automatically and/or at least substantially at the same time or immediately during the taking of the sample or on oral contact with the animal 3. In particular, at least larger or coarser particles and/or contaminants in the saliva 2 are filtered or deposited on the surface of the casing 9 and/or in the casing 9, preferably at least substantially immediately during the sampling and/or while it is still in the mouth 4 of the animal 3.

Preferably, particles and/or contaminants which are larger than 50 µm or 100 µm, particularly preferably larger than 150 µm or 250 µm, particularly larger than 500 µm or 1000 µm, are filtered or deposited on the surface of the casing 9 and/or in the casing 9.

Preferably, the saliva 2 or the sample material 11 purified by means of the casing 9 is taken up, particularly absorbed, by the core 8.

Preferably, it is possible, by means of the proposed method or the proposed use of the core of a rope, to purify or filter the saliva 2 or the sample material 11 taken, at least substantially directly or simultaneously with the taking of the saliva sample 2 or during oral contact with the animal 3 or in the mouth 4 of the animal 3. In particular, the saliva 2 or the sample material 11 is purified or filtered automatically or as a result of the chewing and/or biting of the receiving device 1.

Preferably, the receiving device 1 is removed from the carrier 5 after the sampling.

Preferably, the receiving device 1 is then opened—particularly at the sides and/or axially or at the ends—in order to remove the core 8 or the core of the rope. Particularly preferably, the closure element 12 of the receiving device 1 is removed from or pulled or twisted off the receiving device 1 or the casing 9, particularly so as to expose the core 8 and/or make it accessible or capable of being gripped.

Alternatively or additionally, the casing 9 is cut open and/or torn open.

Preferably, the core 8 is then removed from or pulled out of the casing 9. Particularly preferably, the receiving device 1 or the rope is gripped or held by means of the handle 13, to enable the core 8 to be removed or pulled out. This provides a particularly simple, rapid and/or hygienic method of removing the core 8.

Preferably, the receiving device 1 or the rope, particularly the core 8, is then—at least partially—placed in the collecting device 16 or bag 17 and/or accommodated by the collecting device 16 or the bag 17.

Alternatively, the core 8 may also be gripped directly by means of the collecting device 16 of the bag 17 and released or pulled out of the casing 9.

The core 8 is then wrung out, squeezed out, spun out and/or pressed out in the collecting device 16 or in the bag 17, particularly manually, so that the filtered saliva 2 or the sample material 11 is at least partially released from the core 8 and/or collects in the collecting device 16, particularly the container 18. Additionally, or alternatively, the saliva 2 or the sample material 11 is eluted or dissolved out of the core 8, preferably using a solvent.

Particularly preferably, the collecting device 16 is closed for this purpose, particularly in order to prevent the collected saliva 2 or the saliva sample 15 obtained in this way from flowing out.

Preferably, the container 18 is separated from the collecting device 16 or the bag 17, particularly pulled off or twisted off. The container 18 may be sealed for better handling or transporting.

Preferably, the saliva sample 15 or the container 18 containing the saliva sample 15 is then taken for immediate or direct veterinary examination, particularly on the spot, preferably with no need for any further processing or filtering of the saliva sample 15.

However, the saliva sample 15 obtained in this way and, in particular, filtered may also be removed directly from the collecting device 16, preferably using a syringe, pipette or the like. Preferably, the sample material 11 thus filtered or the saliva sample 15 is examined directly or immediately, preferably for diseases and/or pathogens, particularly microorganisms and/or antibodies.

Individual aspects and features of the proposed invention may be implemented independently of one another, but also in any desired combination or sequence.

The invention claimed is:
1. A receiving device for receiving saliva from an animal, comprising:
 (1) a rope having, (a) a core and (b) a casing, the casing surrounding the core, and
 (2) a closure element covering a grippable end of the core that is exposed relative to the casing,
 wherein the casing is constructed to enable the core to be at least partially nondestructive pulled from the casing upon removal of the closure element for examination of saliva obtained from the mouth of an animal.

2. The receiving device according to claim 1, wherein the receiving device is at least one of flexible, elastic and bite-proof.

3. The receiving device according to claim 1, wherein the casing is permeable, and wherein the core is formed of a material that absorbs fluids or saliva more than the casing.

4. The receiving device according to claim 1, wherein the casing is configured to separate the saliva and accompanying particles from one another.

5. The receiving device according to claim 1, wherein at least one of the core and the casing are made of natural or synthetic fibers that are digestible or biodegradable.

6. The receiving device according to claim 1, wherein the core and the casing are made from the same material.

7. A kit for obtaining a filtered saliva sample from an animal, comprising:
 receiving device in the form of a rope having a core, a casing, and a removable closure element, the casing surrounding the core except for a grippable end which is covered by the closure element, and wherein casing is constructed in a manner enabling the core to be at least partially nondestructively pulled from the casing after removal of the closure element for examination of the saliva,
 a collecting device for collecting saliva from the core, and
 a packaging containing the receiving and collecting devices.

8. A method for obtaining a saliva sample from an animal, comprising:
 arranging for an animal to put a receiving device in its mouth that is in the form of a rope having a core and a casing surrounding the core except for a grippable end of the core which is covered by a closure element,
 filtering saliva from the animal by means of the casing with particles adhering to the casing and the saliva passing through the casing to the core,
 removing the closure element and at least partially removing the core from the casing in a nondestructive manner by pulling on said grippable end of the core, and
 extracting the saliva from the at least partially removed core into a collecting device.

9. The method according to claim 8, wherein the filtering of the saliva of the animal is produced by the casing being permeable.

10. The method according to claim 8, wherein said extracting of the saliva from the core is performed by the at least partially removed core being wrung, squeezed or spun so as to at least partially release the saliva from the core.

11. The method according to claim 8, wherein the saliva sample is obtained from a pig.

12. The method according to claim 8, wherein the saliva is absorbed by the core as a result of oral contact of the animal with the receiving device by at least one of chewing and biting of the receiving device.

13. The method according to claim 8, wherein the rope is pulled out completely from the casing after absorbing the saliva.

* * * * *